(12) United States Patent
Clevenger et al.

(10) Patent No.: US 10,876,217 B2
(45) Date of Patent: Dec. 29, 2020

(54) ELECTROCHEMICAL ATTACHMENT OF PHOSPHONIC ACIDS TO METALLIC SUBSTRATES AND OSTEOCONDUCTIVE MEDICAL DEVICES CONTAINING SAME

(71) Applicant: Molecular Surface Technologies, LLC, Eatontown, NJ (US)

(72) Inventors: Randell Clevenger, North Plainfield, NJ (US); Gordon D. Donald, Oceanport, NJ (US)

(73) Assignee: Molecular Surface Technologies, LLC, New Brunswick, NJ (US)

( * ) Notice: Subject to any disclaimer, the term of this patent is extended or adjusted under 35 U.S.C. 154(b) by 0 days.

(21) Appl. No.: 16/383,263

(22) Filed: Apr. 12, 2019

(65) Prior Publication Data

US 2020/0109483 A1   Apr. 9, 2020

Related U.S. Application Data

(60) Provisional application No. 62/657,274, filed on Apr. 13, 2018.

(51) Int. Cl.
  *C25D 9/02*   (2006.01)
  *C25D 9/06*   (2006.01)
  *C07K 1/00*   (2006.01)
  *C07K 14/51*  (2006.01)

(52) U.S. Cl.
  CPC ............ *C25D 9/02* (2013.01); *C07K 1/00* (2013.01); *C25D 9/06* (2013.01); *C07K 14/51* (2013.01)

(58) Field of Classification Search
  CPC .................................. C25D 9/02; C25D 9/06
  See application file for complete search history.

(56) References Cited

U.S. PATENT DOCUMENTS

| 4,166,776 A | 9/1979 | Lefebvre et al. |
| 5,032,237 A | 7/1991 | Wiserman et al. |
| 5,102,507 A | 4/1992 | Wieserman et al. |
| 5,126,210 A | 6/1992 | Wieserman et al. |
| 5,277,788 A | 1/1994 | Nitowski et al. |
| 6,146,767 A | 11/2000 | Schwartz |

(Continued)

FOREIGN PATENT DOCUMENTS

CN   106237376   6/2019

OTHER PUBLICATIONS

Anitha et al., Synthesis, characterization, cytotoxicity and antibacterial studies of chitosan, O-carboxymethyl and N,O-carboxymethyl chitosan nanoparticles, Carbohydrate Polymers, 2009, 78, pp. 672-677.

(Continued)

*Primary Examiner* — Brian W Cohen
(74) *Attorney, Agent, or Firm* — Dentons US LLP

(57) ABSTRACT

A method of preparing a modified-metal surface by attaching a phosphorous-based acid to a surface of a metal: preparing a solution of the phosphorous-based acid in a protic solvent; immersing a strip of a metal work piece into the solution of the phosphorous-based acid, immersing a strip of a reference metal into the solution of the phosphorous-based acid, supplying a voltage for a duration of time, removing the metal work piece, cleaning the metal work piece, and drying the cleaned metal work piece under an inert atmosphere to obtain a modified metal work piece.

19 Claims, 2 Drawing Sheets

(56) References Cited

U.S. PATENT DOCUMENTS

| | | | |
|---|---|---|---|
| 6,645,644 | B1 | 11/2003 | Schwartz et al. |
| 7,396,594 | B2 | 7/2008 | Schwartz et al. |
| 7,507,483 | B2 | 3/2009 | Schwartz et al. |
| 7,569,285 | B2 | 8/2009 | Schwartz et al. |
| 7,815,963 | B2 | 10/2010 | Schwartz et al. |
| 7,879,456 | B2 | 2/2011 | Schwartz et al. |
| 7,931,943 | B2 | 4/2011 | Schwartz et al. |
| 8,092,585 | B2 | 1/2012 | Schwartz et al. |
| 9,868,808 | B2 | 1/2018 | Clevenger et al. |
| 10,390,533 | B2 | 8/2019 | Clevenger |
| 10,449,750 | B2 * | 10/2019 | Caicedo-Carvajal ........................ C09J 175/14 |
| 2004/0023048 | A1 | 2/2004 | Schwartz et al. |
| 2006/0073280 | A1 | 4/2006 | Bauer et al. |
| 2008/0206443 | A1 | 8/2008 | Schwartz et al. |
| 2009/0004481 | A1 | 1/2009 | Schwartz et al. |
| 2010/0167072 | A1 | 7/2010 | Chouai et al. |
| 2010/0215643 | A1 | 8/2010 | Clevenger et al. |
| 2011/0100081 | A1 | 5/2011 | Rau et al. |
| 2015/0132470 | A1 | 5/2015 | Namba |
| 2016/0168725 | A1 | 6/2016 | Pfirrmann et al. |
| 2017/0292064 | A1 | 10/2017 | Monroe et al. |

OTHER PUBLICATIONS

Arnold et al., Efficacy of i-Factor Bone Graft versus Autograft in Anterior Cervical Discectomy and Fusion, Spine, 2016, vol. 41, No. 13, pp. 1075-1083.

Borchard, Chitosans for gene delivery, Advanced Drug Delivery Reviews, 2001, 52, pp. 145-150.

Dubey et al., Characterization of self-assembled organic films using differential charging in X-ray photoelectron spectroscopy, Langmuir, 2006, 22 (10), pp. 4649-4653.

Dubey et al., Structure and Order of Phosphonic Acid-Based Self-Assembled Monolayers on Si(100), Langmuir, 2010, 26 (18), pp. 14747-14754.

Franking et al., Highly Stable Molecular Layers on Nanocrystalline Anatase TiO2 through Photochemical Grafting, Langmuir, 2009, 25 (18), pp. 10676-10684.

Galoppini, Linkers for anchoring sensitizers to semiconductor nanoparticles, Coordination Chemistry Reviews (2004), 248, pp. 1283-1297.

Gao et al., Solid-State Nmr-Studies of Self-Assembled Monolayers, Langmuir, 1995, 11, pp. 1860-1863.

Gawalt et al., Enhanced bonding of alkanephosphonic acids to oxidized titanium using surface-bound alkoxyzirconium complex interfaces, Langmuir, 1999, 15 (26), pp. 8929-8933.

Gawalt et al., Enhanced bonding of organometallics to titanium via a titanium(III) phosphate interface, Langmuir, 2001; 17 (21), pp. 6743-6745.

Gawalt et al., Self-assembly and bonding of alkanephosphonic acids on the native oxide surface of titanium, Langmuir, 2001; 17 (19), pp. 5736-5738.

Gouzman et al., Monolayer vs. multilayer self-assembled alkylphosphonate films: X-ray photoelectron spectroscopy studies, Surface Science, 2006; 600, pp. 773-781.

Hanson et al., Bonding self-assembled, compact organophosphonate monolayers to the native oxide surface of silicon, J. Am. Chem. Soc., 2003, 125 (51), pp. 16074-16080.

Hirano et al., Effects of chitosan, pectic acid, lysozyme, and chitinase on the growth of several phytopathogens, Agricultural and Biological Chemistry, 1989, 53 (11), pp. 3065-3066.

International Search Report and Written Opinion dated Jun. 25, 2019 in related Application No. PCT/US19/27330 filed Apr. 12, 2019 (9 pages).

International Search Report and Written Opinion dated Apr. 28, 2020 in related Application No. PCT/US19/68579 filed Dec. 26, 2019 (19 pages).

Jayakumar et al., Bioactive and metal uptake studies of carboxymethyl chitosan-graft-D-glucuronic acid membranes for tissue engineering and environmental applications, International Journal of Biological Macromolecules, 2009, 45, pp. 135-139.

Jayakumar et al., Chitosan conjugated DNA nanoparticles in gene therapy, Carbohydrate Polymers, 2010, 79, pp. 1-8.

Jayakumar et al., Novel chitin and chitosan nanofibers in biomedical applications, Biotechnology Advances, 2010, 28, pp. 142-150.

Jennings et al., Chitosan Based Biomaterials, vol. 1: Fundamentals, 2017, Elsevier (323 pages).

Jennings et al., Chitosan Based Biomaterials, vol. 2: Tissue Engineering and Therapeutics, 2017, Elsevier (278 pages).

Kasaj et al., Clinical evaluation of anorganic bovine-derived hydroxyapatite matrix/cell-binding peptide (P-15) in the treatment of human infrabony defects., Clin Oral Invest, 2008, 12, pp. 241-247.

Liu et.al., Covalent attachment of P15 peptide to titanium surfaces enhances cell attachment, spreading, and osteogenic gene expression, Journal of Orthopaedic Research, 2012, pp. 1-9.

Madhumathi et al., Development of novel chitin/nanosilver composite scaffolds for wound dressing applications, Journal of Materials Science: Materials in Medicine, 2010, 21, pp. 807-813.

Prabaharan, Review paper: chitosan derivatives as promising materials for controlled drug delivery, Journal of Biomaterials Applications, 2008, 23, pp. 5-36.

Pubchem, Substand Record for SID 234146215, available Feb. 12, 2015, retrieved Mar. 30, 2020, https://pubchem.ncbi.nlm.nih.gov/substance/234146215.

Pujari et al., Covalent Surface Modification of Oxide Surfaces, Angew. Chem. Int. Ed. (2014), 53, pp. 2-36.

Sherman et al., Evaluation of ABM/P-15 versus autogenous bone in an ovine lumbar interbody fusion model., Eur Spine J, 2010, 19, pp. 2156-2163.

Tiwari et al., Electrochemical synthesis of chitosan-co-polyaniline/ WO3—nH2O composite electrode for amperometric detection of NO2 gas, Electroanalysis 20, 2008, 16, pp. 1775-1781.

Weber et al., Glycosylidene Carbenes, Helvetica Chimica Acta, 1998, 81, pp. 1359-1372.

Woodward et al., Self-assembled monolayer growth of octadecylphosphonic acid on mica, Langmuir, 1996, 12, pp. 3626-3629.

Yukna et al., Multi-center clinical evaluation of combination anorganic bovine-derived hydroxyapatite matrix (ABM)/cell binding peptide (P-15) as a bone replacement graft material in human periodontal osseous defects. 6-month results., J Periodontol. 1998, 69, pp. 655-663.

Azom, Medical Applications of Stainless Steel 304, Aug. 2012, https://www.azom.com/article.aspx?ArticleID=6641#:~:text=Medical%20Applications%20for%20Stainless%20Steel.hygiene%20is%20of%20particular%20importance (4 pages).

Heinze et al., Electrochemistry of Conducting Polymers—Persistent Models and New Concepts, Chem Rev, 2010, pp. 4724-4771.

International Search Report and Written Opinion dated Sep. 28, 2020 in Application No. PCT/US20/38688 filed Jun. 19, 2020 (12 pages).

Pauls, Chitosan as an Antiviral, May 2016 https://scholarworks.uark.edu/cgi/viewcontent.cgi?article=1029&context=bmeguht (23 pages).

Wikipedia Quartz Microcrystal Balance, Oct. 2018 (19 pages).

Yukna et al., Thirty-six month follow-up of 25 patients treated with combination anorganic bovine-derived hydroxyapatite matrix (ABM)/cell-binding peptide (P-15) bone replacement grafts in human infrabony defects. I. Clinical findings., J Periodontol. 2002, 73, pp. 123-128.

\* cited by examiner

ELECTROCHEMICAL ATTACHMENT OF PHOSPHONIC ACIDS TO METALLIC SUBSTRATES AND OSTEOCONDUCTIVE MEDICAL DEVICES CONTAINING SAME

CROSS REFERENCE TO RELATED APPLICATIONS

The present application claims the benefit of U.S. Provisional Application Ser. No. 62/657,274 filed 13 Apr. 2018, which is incorporated herein by reference in its entirety

BACKGROUND

Phosphonic are the gold standard for surface modifications of metallic substrates. Phosphates, phosphonates and phosphinates form strong hydrolytically stable bonds with metallic surfaces by bonding to the oxide layer which exists on said surfaces. The oxide layer can either be the native oxide layer that forms spontaneously in air or an oxide layer formed by a process such as anodization.

Conventionally[2-9,13], phosphonic acids are attached to metals by forming a chemisorbed layer and driving chemical attachment of said layer to the metal surface. The chemisorbed layer is formed by soaking or spraying the phosphonic acid on the metal surface. Chemical attachment is generally achieved by application of heat. The heating step is, conventionally, carried out at around 130° C. for 18 to 36 hours. The heating may be reduced to about 4 hours by baking at 170° C. for four hours. Alternatively, as described in U.S. Pat. No. 5,126,210, anodization (under aqueous conditions) may be used to attach short water soluble phosphonic acids to aluminum. However, the process described in U.S. Pat. No. 5,126,210 is limited to phosphonic acids having carbon chain lengths no longer than three carbons, because phosphonic acids with chain lengths longer than three carbons are typically insoluble in water.

Metallic surfaces bonded to a phosphonic acid overlayer may be used in osteoconductive medical devices, including, but not limited to, orthopedic implants.

Titanium as a material for orthopedic implants has many advantages. Titanium has a low elastic modulus, is corrosion resistant, and its stable oxide layer makes it relatively inert in the body, as well as biocompatible. However, a significant percentage of titanium implants fail to integrate with the surrounding bone. This is especially significant in patients with risk factors such as smoking, diabetes or osteoporosis. Non-integration often leads to revision surgery which can cause additional pain and suffering to the patient and is associated with an increased chance of infection. Thus, there is a continuing need for enhancement of the ability of metallic implants to integrate with surrounding tissue.

Many strategies have been tried to enhance the osteointegration of medical devices, including the use of bone morphogenetic proteins (BMP), and various osteogenic peptides mixed with a variety of delivery formats. P15 is a short fifteen amino acid peptide (GTPGPQGIAGQRGVV), which captures the integrin binding domain of type I collagen. It has been shown that when P15 is mixed with anorganic bone matrix (ABM) and immobilized on both polymeric and metallic surfaces, the P15 enhances and accelerates osteoblast attachment and spreading. P15 also increases the expression of the $\alpha_2$ integrin protein and initiates osteoblast differentiation. P15's ability to enhance bone formation is well established in scientific literature.[1,10,12,14,15] For example, Liu et al.[11] demonstrated the potential utility of chemical attachment of the peptide to an implant surface.

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

While certain aspects of conventional technologies have been discussed to facilitate disclosure of the invention, the inventors of this application in no way disclaim these technical aspects, and it is contemplated that the claimed invention may encompass or include one or more of the conventional technical aspects discussed herein.

SUMMARY OF INVENTION

An inventive aspect of this application aims to address the drawbacks associated with conventional methods for attaching phosphonic acids to a metal. Longer more complex phosphonic acids, such as phosphonic acids having chain lengths of about three carbon atoms or longer, can be attached to a metal, such as titanium, aluminum and the like, by the method described herein, because such phosphonic acids are soluble in an organic solvent. An example of such organic solvents includes, but is not limited to, alcohols, tetrahydrofuran (THF), demethylformamide (DMF), and the like.

An exemplary embodiment of this application is directed to a method of preparing a modified-metal surface by attaching a phosphorous-based acid to a surface of a metal. The method comprises: preparing a solution of the phosphorous-based acid in a solvent; immersing a strip of a metal work piece into the solution of the phosphorous-based acid; immersing a strip of a reference metal into the solution of the phosphorous-based acid; supplying a voltage for a duration of time; removing the metal work piece; cleaning the metal work piece; and drying the cleaned metal work piece to obtain a modified metal work piece. The atmosphere under which the cleaned metal work piece is dried is not limited, and may include an inert atmosphere, dry air, and the like.

In another exemplary embodiment, the phosphorous-based acid is a phosphonic acid, a phosphoric acid, a phosphinic acid, or mixtures thereof In another exemplary embodiment, the phosphorous-based acid is a phosphonic acid having the following formula: $(OH)_2P(O)(RX)$, wherein R is an alkyl group having more than three carbon atoms, and X is selected from the group consisting of a substituted or unsubstituted hydroxyl group, a substituted or unsubstituted amine group, and a substituted or unsubstituted ester group.

In another exemplary embodiment, the phosphorous-based acid is a phosphonic acid having the following formula: $(OH)_2P(O)(RX)$, wherein R is an alkyl group having four carbon atoms, five carbon atoms, six carbon atoms, seven carbon atoms, eight carbon atoms, nine carbon atoms, ten carbon atoms, eleven carbon atoms, twelve carbon atoms, thirteen carbon atoms, fourteen carbon atoms, fifteen carbon atoms, sixteen carbon atoms, seventeen carbon atoms, eighteen carbon atoms, nineteen carbon atoms, twenty carbon atoms, twenty-one carbon atoms, twenty-two carbon atoms, twenty-three carbon atoms, twenty-four carbon atoms, or twenty-five carbon atoms.

In another exemplary embodiment, X is a substituted or unsubstituted methacrylate group.

In another exemplary embodiment, the phosphonic acid is selected from the group consisting of octadecylphosphonic acid, decaphosphonic acid, and dodecaphosphonic acid.

In another exemplary embodiment, the metal is a non-ferrous metal.

In another exemplary embodiment, the metal is selected from the group consisting of Ti, Zr, Hf, V, Nb, Ta, Al, and alloys thereof.

In another exemplary embodiment, the metal is selected from the group consisting of titanium, titanium alloys, aluminum and aluminum alloys.

In another exemplary embodiment, the solvent is selected from the group consisting of methanol, ethanol, tetrahydrofuran (THF), demethylformamide (DMF), and mixtures thereof.

In another exemplary embodiment the concentration of the solution is from about 1% to about 10% solution by weight. In another exemplary embodiment the concentration of the solution is about 1%, about 2%, about 3%, about 4%, about 5%, about 6%, about 7%, about 8%, about 9%, about 10%, about 11%, about 12%, about 13%, about 14%, or about 15%.

In another exemplary embodiment, the voltage applied may range from about 1 V to about 300 V. In another exemplary embodiment, the voltage applied may be about 10 V, about 20 V, about 30 V, about 40 V, about 50 V, about 60 V, about 70 V, about 80 V, about 90 V, about 100 V, about 110 V, about 120 V, about 130 V, about 140 V, about 150 V, about 160 V, about 170 V, about 180 V, about 190 V, about 200 V, about 210 V, about 220 V, about 230 V, about 240 V, about 250 V, about 260 V, about 270 V, about 280 V, about 290 V or about 300 V.

In another exemplary embodiment, the voltage applied may range from about 1 V to about 100 V. In another exemplary embodiment, the voltage applied may be about 1 V, about 2 V, about 3 V, about 4 V, about 5 V, about 6 V, about 7 V, about 8 V, about 9 V, about 10 V, about 11 V, about 12 V, about 13 V, about 14 V, about 15 V, about 16 V, about 17 V, about 18 V, about 19 V, about 20 V, about 21 V, about 22 V, about 23 V, about 24 V, about 25 V, about 26 V, about 27 V, about 28 V, about 29 V, about 30 V, about 31 V, about 32 V, about 33 V, about 34 V, about 35 V, about 36 V, about 37 V, about 38 V, about 39 V, about 40 V, about 41 V, about 42 V, about 43 V, about 44 V, about 45 V, about 46 V, about 47 V, about 48 V, about 49 V, about 50 V, about 51 V, about 52 V, about 53 V, about 54 V, about 55 V, about 56 V, about 57 V, about 58 V, about 59 V, about 60 V, about 61 V, about 62 V, about 63 V, about 64 V, about 65 V, about 66 V, about 67 V, about 68 V, about 69 V, about 70 V, about 71 V, about 72 V, about 73 V, about 74 V, about 75 V, about 76 V, about 77 V, about 78 V, about 79 V, about 80 V, about 81 V, about 82 V, about 83 V, about 84 V, about 85 V, about 86 V, about 87 V, about 88 V, about 89 V, about 90 V, about 91 V, about 92 V, about 93 V, about 94 V, about 95 V, about 96 V, about 97 V, about 98 V, about 99 V, or about 100 V.

In another exemplary embodiment, the duration of time is from about 1 second to about 5 minutes. In another exemplary embodiment, the duration of time is about 1 second, about 5 seconds, about 10 seconds, about 15 seconds, about 20 seconds, about 25 seconds, about 30 seconds, about 35 seconds, about 40 seconds, about 45 seconds, about 50 seconds, about 55 seconds, about 60 seconds, about 65 seconds, about 70 seconds, about 75 seconds, about 80 seconds, about 85 seconds, about 90 seconds, about 95 seconds, about 100 seconds, about 105 seconds, about 110 seconds, about 115 seconds, about 120 seconds, about 130 seconds, about 140 seconds, about 150 seconds, about 160 seconds, about 170 seconds, about 180 seconds, about 190 seconds, about 200 seconds, about 210 seconds, about 220 seconds, about 230 seconds, about 240 seconds, about 250 seconds, about 260 seconds, about 270 seconds, about 280 seconds, about 290 seconds, about 300 seconds, about 6 minutes, about 7 minutes, about 8 minutes, about 9 minutes, or about 10 minutes.

In another exemplary embodiment, the inert atmosphere comprises any nonreactive gas. In another exemplary embodiment, the inert atmosphere is nitrogen or argon.

In another exemplary embodiment, a coefficient of friction of the modified-metal surface is up to 99% lower than a coefficient of friction of an untreated metal surface. In another exemplary embodiment, a coefficient of friction of the modified-metal surface is up to 95% lower than a coefficient of friction of an untreated metal surface. In another exemplary embodiment, a coefficient of friction of the modified-metal surface is up to 90% lower than a coefficient of friction of an untreated metal surface, and the like.

In another exemplary embodiment, a coefficient of friction of the modified-metal surface is about 34% to about 59% lower than a coefficient of friction of an untreated metal surface. In another exemplary embodiment, a coefficient of friction of the modified-metal surface is about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, or about 59% lower than a coefficient of friction of an untreated metal surface.

In another exemplary embodiment, a static coefficient of friction of the modified-metal surface is up to 99% lower than a coefficient of friction of an untreated metal surface. In another exemplary embodiment, a static coefficient of friction of the modified-metal surface is up to 95% lower than a coefficient of friction of an untreated metal surface. In another exemplary embodiment, a static coefficient of friction of the modified-metal surface is up to 90% lower than a coefficient of friction of an untreated metal surface, and the like.

In another exemplary embodiment, a static coefficient of friction of the modified-metal surface is about 34% to about 46% lower than a static coefficient of friction of an untreated metal surface. In another exemplary embodiment, a static coefficient of friction of the modified-metal surface is about 30%, about 31%, about 32%, about 33%, about 34%, about 35%, about 36%, about 37%, about 38%, about 39%, about 40%, about 41%, about 42%, about 43%, about 44%, about 45%, or about 46% lower than a static coefficient of friction of an untreated metal surface.

In another exemplary embodiment, a dynamic coefficient of friction of the modified-metal surface is up to 99% lower than a coefficient of friction of an untreated metal surface. In another exemplary embodiment, a dynamic coefficient of friction of the modified-metal surface is up to 95% lower than a coefficient of friction of an untreated metal surface. In another exemplary embodiment, a dynamic coefficient of friction of the modified-metal surface is up to 90% lower than a coefficient of friction of an untreated metal surface, and the like.

In another exemplary embodiment, a dynamic coefficient of friction of the modified-metal surface is about 50% to about 59% lower than a dynamic coefficient of friction of an untreated metal surface. In another exemplary embodiment, a dynamic coefficient of friction of the modified-metal surface is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, or about 59% lower than a dynamic coefficient of friction of an untreated metal surface.

Another exemplary embodiment of this application is directed to a method for producing a peptide- or protein-modified metal, the method comprising: attaching a phosphorous-based acid to a surface of the metal according to claim 1; carrying out a coupling reaction between the phosphorous-based acid and the carboxyl end of the peptide or protein; and deprotection after coupling to obtain the peptide or protein-modified metal.

In another exemplary embodiment, the phosphorous-based acid is (2-(2-(2-(2-aminoethoxy)ethoxy)ethoxy)ethyl) phosphonic acid.

In another exemplary embodiment, the protein is a bone morphogenetic protein.

In another exemplary embodiment, the peptide is P15.

Another exemplary embodiment of this application is directed to a method of modifying a polymer, a biopolymer or a ceramic material by attaching a phosphorous-based acid to a surface of the polymer, the biopolymer or the ceramic material, the method comprising: preparing a solution of the phosphorous-based acid in a solvent; immersing a strip of a work piece comprising the polymer, the biopolymer or the ceramic material into the solution of the phosphorous-based acid; immersing a strip of a reference material into the solution of the phosphorous-based acid; supplying a voltage for a duration of time; removing the work piece; cleaning the work piece; and drying the cleaned work piece to obtain a modified work piece.

Details of other exemplary embodiments of the present disclosure will be included in the following detailed description and the accompanying drawings.

DETAILED DESCRIPTION

Figure 1:
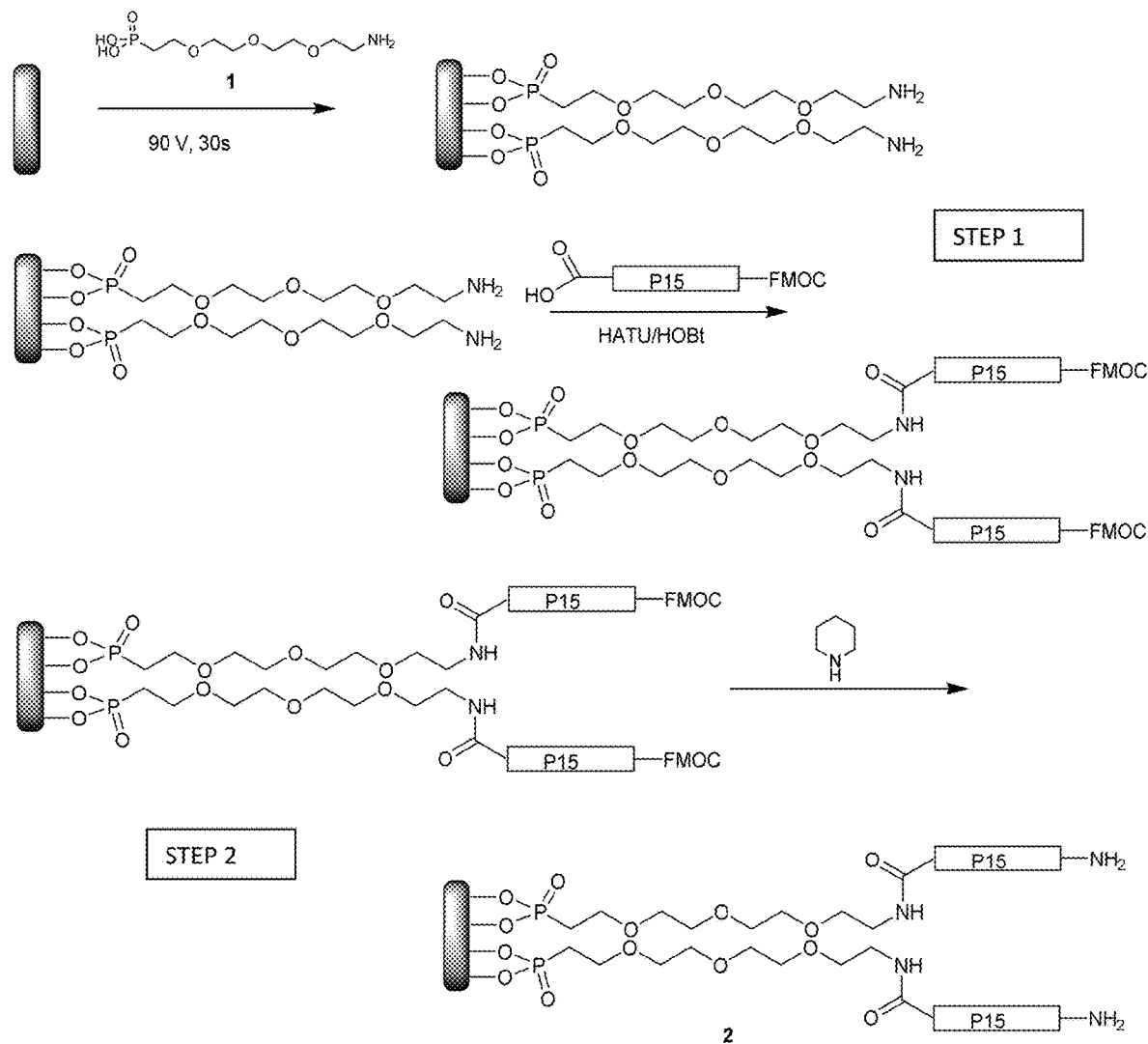
FIG. 1 shows an exemplary two-step process for immobilizing P15.

Advantages and features of the present disclosure, and methods for accomplishing the same will be more clearly understood from exemplary embodiments described below with reference to the accompanying drawings. However, the present disclosure is not limited to the following exemplary embodiments and may be implemented in various different forms. The exemplary embodiments are provided only to complete disclosure of the present disclosure and to fully provide a person having ordinary skill in the art to which the present disclosure pertains with the category of the invention, and the present disclosure will be defined by any appended claims and combinations thereof Shapes, sizes, ratios, angles, numbers, and the like shown in the accompanying drawings are merely exemplary, and the present disclosure is not limited thereto. Like reference numerals generally denote like elements throughout the present specification. Further, in the following description, a detailed explanation of well-known related technologies may be omitted to avoid unnecessarily obscuring the subject matter of the present disclosure. Terms such as "including," "having," and "consisting of" used herein are generally intended to allow other components to be included unless the terms are used in conjunction with the term "only." Any references to the singular may include the plural unless expressly stated otherwise.

Components are interpreted to include an ordinary error range even if not expressly stated.

As used herein, the singular forms "a," "an" and "the" are intended to include the plural forms as well, unless the context clearly indicates otherwise. Additionally, the use of "or" is intended to include "and/or," unless the context clearly indicates otherwise.

When the positional relation between two parts is described using the terms such as "on," "above," "below," and "next," one or more parts may be positioned between the two parts unless the terms are used in conjunction with the term "immediately" or "directly."

When an element or layer is referred to as being "on" another element or layer, the element or layer may be directly on the other element or layer, or intervening elements or layers may be present.

Although the terms "first," "second," and the like are used for describing various components, these components are not confined by these terms. These terms are merely used for distinguishing one component from the other components, and a first component may be a second component in a technical concept of the present disclosure.

The size and thickness of each component illustrated in the drawings are represented for convenience of explanation, and the drawings are not necessarily to scale.

The features of various embodiments of the present disclosure can be partially or entirely bonded to or combined with each other and can be interlocked and operated in various technical ways, and the embodiments can be carried out independently of, or in association with, each other.

Hereinafter, various exemplary embodiments of the present disclosure will be described in detail with reference to the accompanying drawings.

The phosphorous-based acids attach to metal surfaces by forming strong P—O-M bonds, where M is a metal, and can serve as interfaces between metallic surfaces and the environment. For example, a phosphonic acid comprises a phosphorous atom with two acidic hydroxyls, a double bonded oxygen and a carbon chain attached to the central phosphorus atom. An exemplary phosphonic acid is represented below:

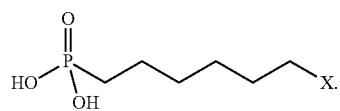

The utility of these functional groups is that the distal end of the organic chain (X) may contain functional groups, which can be further modified. This allows for the installation of a variety of chemistries onto the distal end of these molecules. Thus, covalent attachment of these molecules followed by installation of custom chemistries is tantamount to the covalent attachment of said chemistries onto the surface. Such functional groups may include, but are not limited to, a substituted or unsubstituted hydroxyl, a substituted or unsubstituted amine, a substituted or unsubstituted ester, a substituted or unsubstituted thiol, a substituted or unsubstituted ether, a substituted or unsubstituted phosphonic acid ester, a substituted or unsubstituted phosphinic acid ester, a substituted or unsubstituted phosphoric acid ester, a substituted or unsubstituted carboxylate, a substituted or unsubstituted acrylate, a substituted or unsubstituted sulfonate, a substituted or unsubstituted sulfinate, a substituted or unsubstituted sulfoxide, a substituted or unsubstituted silane, a substituted or unsubstituted siloxane, a substituted or unsubstituted polydimethylsiloxane (PDMS), a substituted or unsubstituted amino ester, a substituted or unsubstituted peptide, both natural and synthetic, a substituted or unsubstituted oligopeptide, proteins, nucleotides, oligonucleotides, polynucleotides, a substituted or unsubstituted sugar, a substituted or unsubstituted polysaccharide, and the like, and these groups may be further modified. The functional group may be an ester, such as a methacrylate, a urethane, a urea, an alkyl halide, and the like.

Manipulating the chemical presentation of a surface to the environment changes the behavior of that surface when compared to an untreated surface. For example, surfaces can be made to be hydrophobic, hydrophilic, oleophobic, lubricious, antimicrobial, and the like. Surfaces may also be made to either enhance or attenuate the effectiveness of adhesives. Further, proteins and protein fragments, amino acids (both natural and synthetic), and peptides may be attached to enhance or attenuate a biological response such as osteointegration.

As discussed earlier in this application, the traditional method for attaching phosphorous-based acids to metallic surfaces is to spray or dip coat a dilute solution onto a metallic surface and thermally drive attachment of the phosphorus-based acids to the metallic surface through heating. In such traditional methods, heating is typically carried out for multiple hours in an oven, at or above about 130° C. Many metal hydroxides are reactive enough to drive attachment of the phosphorous-based acids without heating while addition of heat increases the efficiency of such reactions. For titanium, however, heat is traditionally an absolute requirement for phosphonic/-phoric/-phinic acid attachment.

As described earlier in this application, U.S. Pat. No. 5,126,210 describes an aqueous technique to modify "valve" metals, such as groups IVB and VB, including but not limited to, Ti, Zr, Hf, V, Nb, Ta, Al, and the like, through anodization using small water soluble phosphonic acids. Other researchers, including an inventor of the subject application, have recently expanded on this idea to include anodization using short water soluble phosphonic acids to build a foundational layer upon which antimicrobial surfaces were constructed, for example, as described in U.S. Provisional Application No. 62/408,913. However, the need for water soluble molecules limits the scope and utility of these techniques for attaching phosphonic acids to a metallic surface.

The inventors of this application have developed methods and compositions which utilize anodization-like condition in organic solvents to attach phosphorous based acids to metals. The solvents may include, but are not limited to: protic solvents, such as alcohols (including n-butanol, isopropanol, ethanol, methanol, and the like), acids (including formic acid, acetic acid, and the like); wet polar aprotic solvents, such as tetrahydrofuran (THF), demethylformamide (DMF), and the like; and ionic liquids. In an exemplary embodiment, the protic solvent may be an alcohol including, but not limited to, ethanol, methanol, ispropanol and n-butanol. In an exemplary embodiment, the ionic liquid may include, but is not limited to, 1-ethyl-3-methylimidazolium dicyanamide, 1-ethyl-3-methylimidazolium thiocyanate, triethylsulphonium bis(trifluoromethylsulfonyl)imide, N-methyl-N-trioctylammonium bis(trifluoromethylsulfonyl)imide, N-butyl-N-methylpyrrolidinium bis(trifluoromethylsulfonyl)imide, 1-ethyl-3-methylimidazolium tetrafluoroborate and 1-ethyl-3-methylimidazolium trifluoromethylsulfonate.

The metal may include any metal that forms a robust native oxide layer, including, but not limited to, titanium, titanium alloys, aluminum and aluminum alloys, vanadium and vanadium alloys, zirconium and zirconium alloys, hafnium and hafnium alloys, niobium and niobium alloys, tantalum and tantalum alloys, tungsten and tungsten alloys, stainless steel, cobalt chrome, and the like. However, the material to which the phosphorous-based acid is attached is not limited, and may include polymers, biological polymers, ceramics, and the like.

An inventive aspect of this application is the ability to reduce the coefficient of friction of a metal surface. Another inventive aspect of this application is the ability to reduce the static coefficient of friction of a metal surface. Yet another inventive aspect of this application is the ability to reduce the dynamic coefficient of friction.

An inventive aspect of this application is a method of attaching phosphonic acids to a metallic surface. The method includes: preparing a solution of phosphonic acid in a protic solvent; immersing a clean strip of non-ferrous metal, and coupling the same to the cathode of a DC power supply; immersing a metal workpiece to be modified in the solution, while ensuring that there is no physical contact between the two pieces; bringing the positive terminal of the power supply into electrical contact with the workpiece; holding for a period of time; and removing the modified workpiece. This process may be followed by successive sonication processes in organic and aqueous solutions, and drying the modified workpiece under an inert atmosphere.

The dried workpiece is then analyzed using standard analysis techniques, including, but not limited to, infrared (IR) spectroscopy, contact angle, X-ray Photoelectron Spectroscopy (XPS), Energy-Dispersive X-ray Spectroscopy (EDX), Atomic Force Microscopy (AFM), Time-of-Flight Secondary Ion Mass Spectrometry (Tof-SIMS), Coefficient of Friction (COF) studies, and combinations thereof.

In the above-described method, the phosphonic acid solution may be prepared using a solvent, such that the concentration of the solution varies from 0.001% to a saturated composition. Preferred concentrations of the solution may range from about 0.1% to about 20% solution by weight, preferably from about 0.5% to 15% solution by weight, more preferably from about 1% to about 10% solution by weight.

The voltage of the DC power supply used in the above-described method may range from about 1 V to about 100 V.

The reaction time, during which the metal work piece is held in the ethanol solution during the supply of electric current, may range from about 1 second to about 30 minutes, from about 1 second to about 5 seconds, from about 1 second to about 10 seconds, from about 1 second to about 15 seconds, from about 1 second to about 20 seconds, from about 1 second to about 30 seconds, from about 1 second to about 1 minute, from about 1 second to about 5 minutes, from about 1 second to about 10 minutes, from about 1 second to about 20 minutes, from about 10 seconds to about 30 minutes; from about 20 seconds to about 20 minutes;

from about 30 seconds to about 10 minutes; or from about 30 second to about 5 minutes.

The inert atmosphere may be nitrogen or argon.

An inventive aspect of this application is a fast and efficient method to attach P15, and other peptides and proteins, to the surface of titanium and other metallic surfaces, as well as to polymers, biological polymers and ceramics. An exemplary two-step process for immobilizing P15 is illustrated in Scheme I below. In this exemplary method, in step 1, (2-(2-(2-(2-aminoethoxy)ethoxy)ethoxy)ethyl)phosphonic acid (1) can be quickly attached to the surface of titanium through electrochemical means as shown. This provides both hydrophilicity to the surface, which is important for osteoblast differentiation, and an amine termination to which the peptide can be coupled. In step 2, is a standard coupling reaction between the anchored amine and the carboxyl end of the peptide using HATU/HOBt ((1-[Bis(dimethylamino)methylene]-1H-1,2,3-triazolo[4,5-b]pyridinium 3-oxid hexafluorophosphate) and hydroxybenzotriazole, respectively), which activates the carboxylic functional group for nucleophilic attack by the amine. Deprotection yields the P15 modified titanium surface (2), Ti-P15.

Example 1: Sample Preparation and Surface Modification

Aluminum sheets were obtained from McMaster Karr and cut into either 10 inch×6 inch rectangles or 2.5 inch×2.5 inch squares. Each aluminum work piece has a machined surface and a side with a mirror finish. Prior to modification, each work piece was sonicated multiple times in a 1% ALCONOX® solution (ALCONOX 30®, manufactured by Glen St., White Plains, N.Y., 10603). Sonication was performed in the ALCONOX® solution until no metal particulate was apparent in the solution, followed by successive sonication in water and ethanol. The larger work pieces (10 inch×6 inch rectangular pieces) were washed with a brush and ALCONOX® solution, followed by extensive water and ethanol rinsing. All cleaned substrates were stored under ethanol until needed.

Two different molecules were applied to the surface of the cleaned aluminum work pieces. The first, octadecylphosphonic acid (ODPA), is a phosphonic acid, $(HO)_2P(O)R$, where R is an eighteen carbon (C18) chain attached to the central phosphorous atom of phosphonic acid. The second, decaphosphonic acid (M-10), is the 10-carbon equivalent of ODPA, i.e., M-10 is a phosphonic acid, $(HO)_2P(O)R$, where R is a ten carbon (C10) chain attached to the central phosphorous atom of phosphonic acid.

The following process was used to modify aluminum surfaces with either ODPA or M-10. A 1% by weight solution of the organic compound (either ODPA or M-10) in ethanol was prepared, and a 2.5 sq. in. of aluminum was immersed in the ethanol solution. A thin strip of titanium was immersed in the same solution and connected to the negative terminal of a DC power supply. The voltage of the DC power supply was set to 60 V, and the aluminum pieces was connected with the positive terminal of the power source to complete the electrochemical circuit. In an alternate embodiment, a voltage of 90 V was applied across the solution for 30 seconds. This set-up was held in place for 1 minute. Then the circuit was broken, and the modified aluminum piece was removed from the ethanol solution. The modified work pieces were then sonicated in both ethanol and water thrice for a duration of 15 min each to remove any non-attached molecules.

Pre- and Post-Sonication IR Spectral Measurements 1 inch×1 inch aluminum squares were cleaned, and 1 wt. % solutions of decaphosphonic acid and octadecylphosphonic acid were prepared in ethanol, as described above. The M-10 and ODPA molecules were attached to the aluminum squares in accordance with the method described above.

The resulting hydrophobic surface had a water contact angle of 102 degrees.

Figure 2:
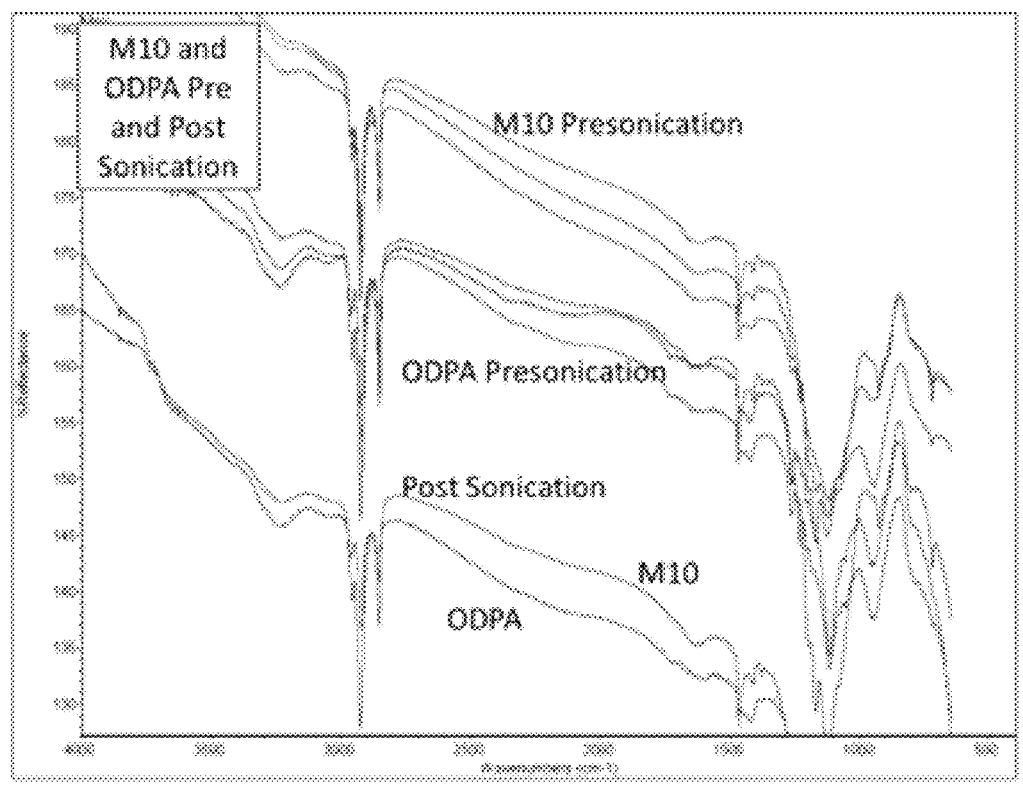
FIG. 2 shows a post-sonication IR spectra of 1×1 inch aluminum squares confirming the persistence of a significant amount of decaphosphonic (M-10) acid and octadecylphosphonic acid (ODPA) bonded to the surface of the aluminum squares.

Attachment of the M-10 and ODPA molecules to the surface of the aluminum squares was confirmed by measuring the infrared spectra of the treated, sonicated and dried samples (pre-sonication spectra of FIG. 2).

The treated samples were subjected to further, exhaustive sonication, including sonication for 15 minutes in ethanol, repeated twice, followed by sonication in PBS buffer (phosphate-buffered saline) for 15 minutes, also repeated twice, to remove any organic material not bonded to the aluminum surface.

As show in FIG. 2, IR spectra of the post-sonication samples demonstrate the persistence of a significant amount of material confirming the strength of the surface modification.

Coefficient of Friction Measurements

The co-efficient of friction was measured on a Mark-10 testing system with the COF force gauge installed. ASTM 1894 was followed in the process described below. A polished 10 inch×6 inch aluminum strip was secured onto the testing sled and served as the common surface for both treated and control aluminum squares. A 200 g weight was used to provide weight as test samples were drawn across the surface of the aluminum strip. Only the polished side of the treated and control squares were evaluated (for example, a polished square (treated or untreated) would be drawn across the polished strip for a distance after which time both the static and dynamic COF would be determined). Each experimental surface was taped to the 200 g sled weight in turn for COF testing. A data run comprised sliding the sled weight to which a test sample had been attached across the aluminum strip for 85 seconds at a rate of 6 in/min as per the ASTM standard. Each data run resulted in one static and one dynamic COF determination, and each condition was run 6 times to generate average static and dynamic COF values.

Figure 3:
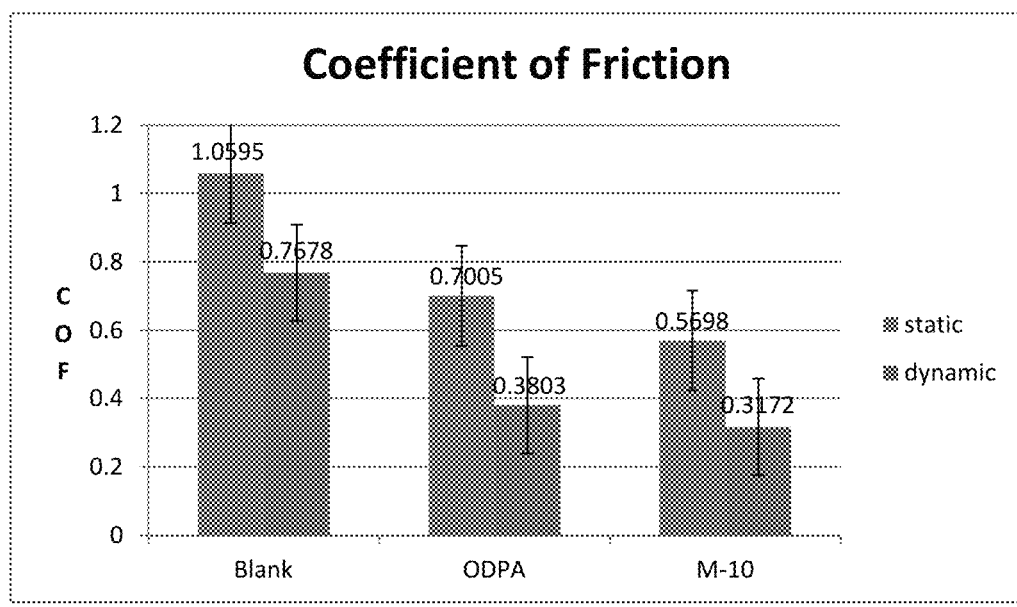
FIG. 3 depicts data showing the reduction in static coefficient of friction (COF) in an aluminum surface coated with ODPA and M-10 compared to an untreated alumina surface.

As shown in FIG. 3, ODPA reduces the static COF of the aluminum surface by 34%, and M-10 reduces it by 46% in this assay, compared to untreated aluminum. The decrease in the dynamic COF of the ODPA- and M-10-treated surfaces are 50% and 59%, respectively, compared to untreated aluminum. A t-test for significance showed that the difference in the means was real with a greater than 95% degree of confidence. It is expected that fluorinated versions of ODPA or M-10 will reduce the COF even further.

Example 2: Modification of Titanium Surface

Titanium foil was cut into 1 inch×3 inch strips and cleaned by successive sonication with alkanox, a degreaser, water and ethanol. The cleaned strips were immersed in a 1% by wt. solution of dodecaphosphonic acid (M-12) in ethanol and connected to the positive terminal of a DC power supply. Another strip of titanium was immersed in the ethanol solution and connected to the negative terminal of the same supply to serve as the cathode. Voltages of 5, 15 and 25 volts were applied for thirty seconds, after which the modified strip of titanium was sonicated in ethanol and water.

Presence of the phosphonic acid on the titanium surface was confirmed by IR spectroscopy which elucidated the C—H stretching peaks at 2854 and 2921 cm$^{-1}$.

Multiple sonications were performed to test the durability of the attachment of M-12 to the titanium surface. After 2 hours, the coating persisted, whereas soaked controls lost all chemisorbed material under the same conditions. Additionally samples were soaked for 7 days in ethanol and 7 days in PBS buffer with no loss of signal in the IR.

TOF-SIMS analysis of treated titanium strips showed the presence of $Ti_xP_yO_z$ fragments in the mass spectrum indicative of covalent attachment of the phosphonic acid to the titanium surface.

Although the exemplary embodiments of the present disclosure have been described in detail with reference to the accompanying drawings, the present disclosure is not limited thereto and may be embodied in many different forms without departing from the technical concept of the present disclosure. Therefore, the exemplary embodiments of the present disclosure are provided for illustrative purposes only and are not intended to limit the technical concept of the present disclosure. The protective scope of the present disclosure should be construed based on any appended claims and combinations thereof, and all the technical concepts in the equivalent scope thereof should be construed as falling within the scope of the present disclosure. As various changes could be made in the above methods and compositions without departing from the scope of the invention, it is intended that all matter contained in the above description shall be interpreted as illustrative and not in a limiting sense. Other embodiments within the scope of the claims herein will be apparent to one skilled in the art from consideration of the specification or practice of the invention as disclosed herein. It is intended that the specification be considered exemplary only, with the scope and spirit of the invention being indicated by the claims.

REFERENCES

1. ARNOLD et al., Efficacy of i-Factor Bone Graft versus Autograft in Anterior Cervical Discectomy and Fusion: Results of the Prospective, Randomized, Single-blinded Food and Drug Administration Investigational Device Exemption Study, Spine (Phila Pa. 1976). 2016 Jul. 1; 41(13), pp 1075-83.
2. DUBEY et al., Structure and Order of Phosphonic Acid-Based Self-Assembled Monolayers on Si(100), Langmuir, 2010, 26 (18), pp 14747-14754.
3. DUBEY et al., Characterization of self-assembled organic films using differential charging in X-ray photoelectron spectroscopy, Langmuir, 2006, 22 (10), pp 4649-4653.
4. GAO et al., Solid-State Nmr-Studies of Self-Assembled Monolayers, Langmuir, 1995, 11 (6), pp 1860-1863.
5. GAWALT et al., Enhanced bonding of alkanephosphonic acids to oxidized titanium using surface-bound alkoxyzirconium complex interfaces, Langmuir, 1999, 15 (26), pp 8929-8933.
6. GAWALT et al., Self-assembly and bonding of alkanephosphonic acids on the native oxide surface of titanium, Langmuir, 2001; 17 (19), pp 5736-5738.
7. GAWALT et al., Enhanced bonding of organometallics to titanium via a titanium(III) phosphate interface, Langmuir, 2001; 17 (21), pp 6743-6745.
8. GOUZMAN et al., Monolayer vs. multilayer selfassembled alkylphosphonate films: X-ray photoelectron spectroscopy studies, Surface Science. 2006; 600 (4), pp 773-781.
9. HANSON et al., Bonding self-assembled, compact organophosphonate monolayers to the native oxide surface of silicon, J. Am. Chem. Soc., 2003, 125 (51), pp 16074-16080.
10. KASAJ et al., Clinical evaluation of anorganic bovine-derived hydroxyapatite matrix/cell-binding peptide (P-15) in the treatment of human infrabony defects., Clin Oral Investig. 2008 September; 12(3), pp 241-7.
11. LIU et. al., Covalent attachment of P15 peptide to titanium surfaces enhances cell attachment, spreading, and osteogenic gene expression, Journal of Orthopaedic Research, 2012, pp 1626-1633.
12. SHERMAN et al., Evaluation of ABM/P-15 versus autogenous bone in an ovine lumbar interbody fusion model., Eur Spine J. 2010 December; 19(12), pp 2156-63.
13. WOODWARD et al., Self-assembled monolayer growth of octadecylphosphonic acid on mica, Langmuir, 1996, 12 (15), pp 3626-3629.
14. YUKNA et al., Multi-center clinical evaluation of combination anorganic bovine-derived hydroxyapatite matrix (ABM)/cell binding peptide (P-15) as a bone replacement graft material in human periodontal osseous defects. 6-month results., J Periodontol. 2000 November; 71(11), pp 1671-9.
15. YUKNA et al., Thirty-six month follow-up of 25 patients treated with combination anorganic bovine-derived hydroxyapatite matrix (ABM)/cell-binding peptide (P-15) bone replacement grafts in human infrabony defects. I. Clinical findings., J Periodontol. 2002 January; 73(1), pp 123-8.

The invention claimed is:

1. A method comprising:
preparing a solution of a phosphorous-based acid in a solvent, wherein the phosphorus-based acid is a phosphonic acid having the formula $(OH)_2P(O)(RX)$,
wherein R is an alky group having between four and twenty-five carbon atoms, and X is selected from the group consisting of a substituted or unsubstituted hydroxyl group, a substituted or unsubstituted amine group, and a substituted or unsubstituted ester group;
immersing at least a portion of a metal work piece into the solution of the phosphorous-based acid;
immersing at least a portion a reference metal into the solution of the phosphorous-based acid;
supplying a voltage for a duration of time, wherein the at least portion of the metal work piece comprises an anode and the at least portion of the reference metal comprises a cathode during the supplying of the voltage;
removing the metal work piece from the solution of the phosphorous-based acid;
cleaning the metal work piece; and
drying the cleaned metal work piece to obtain a surface modified metal work piece.

2. The method according to claim 1, wherein X is a substituted or unsubstituted methacrylate group.

3. The method of claim 1, wherein the phosphonic acid is selected from the group consisting of octadecylphosphonic acid, decylphosphonic acid, and dodecylphosphonic acid.

4. The method according to claim 1, wherein the metal work piece is a non-ferrous metal.

5. The method according to claim 4, wherein the metal work piece is selected from the group consisting of Ti, Zr, Hf, V, Nb, Ta, Al and alloys thereof.

6. The method according to claim 5, wherein the metal work piece is selected from the group consisting of titanium, titanium alloys, aluminum and aluminum alloys.

7. The method according to claim 1, wherein the metal work piece is stainless steel.

8. The method according to claim 1, wherein the solvent is selected from the group consisting of n-butanol, isopropanol, ethanol, methanol, formic acid, acetic acid, tetrahydrofuran (THF), dimethylformamide (DMF), and ionic liquids.

9. The method according to claim 1, wherein the concentration of the phosphorus-based acid in the solution is from about 1% to about 10% by weight.

10. The method according to claim 1, wherein the voltage range is from about 1 V to about 300 V.

11. The method according to claim 10, wherein the voltage range is from about 1 V to about 100 V.

12. The method according to claim 1, wherein the duration of time is from about 1 second to about 5 minutes.

13. The method according to claim 1, wherein drying the cleaned metal work piece is carried out in an inert atmosphere or dry air.

14. The method according to claim 1, wherein a coefficient of friction of the surface modified metal work piece is up to 99% lower than a coefficient of friction of an untreated metal surface.

15. The method according to claim 14, wherein the coefficient of friction of the surface modified metal work piece is about 34% to about 59% lower than a coefficient of friction of an untreated metal surface.

16. The method according to claim 1, wherein a static coefficient of friction of the surface modified metal work piece is up to 99% lower than a static coefficient of friction of an untreated metal surface.

17. The method according to claim 16, wherein the static coefficient of friction of the surface modified metal work piece is about 34% to about 46% lower than a static coefficient of friction of an untreated metal surface.

18. The method according to claim 1, wherein a dynamic coefficient of friction of the surface modified metal work piece is up to 99% lower than a dynamic coefficient of friction of an untreated metal surface.

19. The method according to claim 18, wherein the dynamic coefficient of friction of the surface modified metal work piece is about 50% to about 59% lower than a dynamic coefficient of friction of an untreated metal surface.

* * * * *